(12) United States Patent
Moseley

(10) Patent No.: US 7,900,501 B2
(45) Date of Patent: Mar. 8, 2011

(54) AIR QUALITY MONITOR

(75) Inventor: Patrick T. Moseley, Chapel Hill, NC (US)

(73) Assignee: Atmospheric Sensors Ltd., Little Thetford, Ely, Cambridgeshire (GB)

( * ) Notice: Subject to any disclaimer, the term of this patent is extended or adjusted under 35 U.S.C. 154(b) by 58 days.

(21) Appl. No.: 11/520,137

(22) Filed: Sep. 13, 2006

(65) Prior Publication Data

US 2007/0144237 A1 Jun. 28, 2007

Related U.S. Application Data

(60) Provisional application No. 60/751,950, filed on Dec. 20, 2005.

(51) Int. Cl.
*G01N 27/12* (2006.01)
(52) U.S. Cl. ......................... 73/31.02; 73/31.06
(58) Field of Classification Search .............. 422/96; 73/31.05, 31.06
See application file for complete search history.

(56) References Cited

U.S. PATENT DOCUMENTS

| | | | | | |
|---|---|---|---|---|---|
| 4,001,756 | A | * | 1/1977 | Heijne | 338/34 |
| 4,033,169 | A | * | 7/1977 | Fujishiro et al. | 73/23.31 |
| 4,387,359 | A | * | 6/1983 | Tien et al. | 338/34 |
| 4,410,632 | A | * | 10/1983 | Dilley et al. | 436/20 |
| 4,542,640 | A | * | 9/1985 | Clifford | 73/31.06 |
| 5,212,692 | A | * | 5/1993 | Itoh | 714/704 |
| 5,298,783 | A | * | 3/1994 | Wu | 257/414 |
| 5,320,577 | A | * | 6/1994 | Tooru et al. | 454/75 |
| 5,602,324 | A | * | 2/1997 | Yanagida et al. | 73/23.2 |
| 5,824,271 | A | * | 10/1998 | Frank et al. | 422/98 |
| 6,004,201 | A | | 12/1999 | Rump | |
| 6,660,231 | B2 | | 12/2003 | Moseley | |

FOREIGN PATENT DOCUMENTS

| | | |
|---|---|---|
| DE | 19515886 | 10/1996 |
| JP | 52/141699 | 11/1977 |
| JP | 60/120239 | 6/1985 |
| JP | 2000/275199 | 10/2000 |
| WO | WO 2004/016922 A2 * | 2/2004 |

OTHER PUBLICATIONS

A.M. Nartowski and A. Atkinson. "Sol-Gel Synthesis of Sub-Micron Titanium-Doped Chromia Powders for Gas Sensing." Journal of Sol-Gel Science and Technology. 26. pp. 793-797. 2003.*

(Continued)

*Primary Examiner* — Lisa M Caputo
*Assistant Examiner* — Punam Roy
(74) *Attorney, Agent, or Firm* — James Creighton Wray; Meera P. Narasimhan

(57) ABSTRACT

An air quality monitor having multiple sensors deployed in an electric circuit returns a single sign indication of atmospheric impurity regardless of whether the impurity gas is of the oxidizing or reducing type. Each sensor employs a gas sensitive material that exhibits a response in the form of a change in electrical resistance of the material in the presence of a gas and that exhibits a negligible response to changes in the moisture content of the atmosphere. A powder is dried and calcined and the result is ground into a fine powder and pressed into a desired shape to make the gas sensitive material. Adding a binder during the pressing and firing the shaped powder results in a gas sensitive material with porosity. Gas is flowed to the gas sensitive material and the resulting change in resistance is measured and returned as a single sign indication of atmospheric impurity.

34 Claims, 1 Drawing Sheet

OTHER PUBLICATIONS

U. Hoefer, J. Frank, M. Fleischer. "High temperature Ga2O3-gas sensors and SnO2-gas sensors: a comparison." Sensors and Actuators B. 78. (2001). Abstract.*

P. T. Moseley, "Solid state gas sensors." Meas. Sci. Technol. 8 (1997) pp. 223-227.*

Moseley et al.; *Oxide Semiconductors: Patterns of Gas Response Behavior according to Material Type*; Chap. 4, Techniques and Mechanisms in Gas Sensing; Adam Hilger Series on Sensors; Bristol, Philadelphia, and New York; ISBN 0-7503-0074-4.

Moseley & Williams: *A Selective Ammonium Sensor*; Sensors and Actuators; B1, (1990) pp. 113-115.

* cited by examiner

AIR QUALITY MONITOR

This application claims the benefit of U.S. Provisional Application No. 60/751,950 filed Dec. 20, 2005, which is hereby incorporated by reference in its entirety.

BACKGROUND TO THE INVENTION

Semiconductor gas sensors function by offering a change in electrical resistance in response to a shift in the local concentration of the gas of interest. In general the resistance of the sensor is some function of the concentration of the target gas. It is generally preferred that the semiconducting materials used should offer a response, which is selective for a particular gas, without interference from other components of the atmosphere, including moisture (relative humidity).

The mechanism operating at temperatures within the range 200-500° C. involves reactions of the molecules of the target gas at the surface of the semiconductor (which is usually a metal oxide) and results in a change in near-surface charge-carrier density. Examples of materials functioning through this mechanism can be employed in the detection and monitoring of either reducing gases (hydrogen, carbon monoxide, methane etc.) or oxidizing gases (nitrogen dioxide, chlorine, ozone etc.) in ambient air. The sign of the response (a resistance increase or a resistance decrease), depends on whether the semi-conducting material used is n-type or p-type.

The present applicant has shown that sensors composed of $W_{0.9}Mo_{0.1}O_3$ provide excellent n-type responses (resistance increases) to the oxidizing gases ozone and NOx with only minimal interference from changes in relative humidity. Applicant has also shown that chromium oxide ($Cr_2O_3$), when doped with a few percent of titanium dioxide, provides p-type responses to the reducing gases, ammonia and hydrogen sulfide (also resistance increases) with little interference from changes in relative humidity.

Of course, air quality can be degraded by the presence of oxidizing gases, by reducing gases, or by both. Any one sensor can only provide information about the presence of either reducing gases or oxidizing gases, however, because the sign of the sensor response to each type is different: a resistance increase in one case and a resistance decrease in the other.

Needs exist for simple detectors that can detect degradation of air quality and provide single indications regardless of the gas causing that degradation.

SUMMARY OF THE INVENTION

The present invention uniquely meets those needs. This invention is a simple means of using two sensors of different types to provide a single indication of degradation of air quality regardless of the type of gas involved in that degradation. The invention also provides an improved formulation for a p-type sensor for reducing gases to be used in this strategy.

The present invention relates to sensors and more particularly to sensors for use in gases and gaseous mixtures. In a preferred embodiment, two sensors are provided that are suitable for use in a gaseous mixture. The sensors each include a gas-sensitive material that is capable of exhibiting a response in the form of an increase or a decrease in electrical resistance of the material in the presence of a gas and that exhibits a small response to changes in the moisture content of the atmosphere. The two sensors are then deployed in a circuit, for example a Wheatstone bridge circuit, that allows a unified indication of atmospheric impurity regardless of whether the impurity gas is of the oxidizing or reducing type.

In another preferred embodiment, the gas sensitive materials are provided with two or more electrodes in communication with the gas sensitive materials and the gas sensitive materials are arranged so as to be capable of being contacted with a gas or gaseous mixture.

A sensor in accordance with the present invention may be used as a gas sensor in quantitative and/or qualitative determinations with gases or gaseous mixtures. The electrodes may be in direct communication with the gas sensitive material by being in contact therewith.

In this application, the term "gas" preferably embraces a gas as such and any material that may be present in a gaseous phase, one example of which is a vapor.

The gas sensitive material is a material which responds to a target gas without being affected by changes in relative humidity. Also, the term "gas sensitive material" means a preferred material which is gas (including vapor) sensitive in respect of an electrical property of the material.

In a preferred embodiment, one of the sensors is a p-type sensor and the other an n-type sensor. Alternatively, two n-type sensors may be used. The p-type sensor may have a gas sensitive material made of, for example, chromium oxide, $Cr_2O_3$, doped with a small amount of a transition metal ion having a valence of greater than 4, or one of the perovskites, $LaFe_{0.95}W_{0.05}O_3$ or $PrFe_{0.95}W_{0.05}O_3$. The n-type sensor might use a gas sensitive material of $W_{0.9}Mo_{0.1}O_3$.

The electrical resistance of the gas sensitive material depends upon the gas or gaseous mixture contacting the gas sensitive material. Thus, by measuring the electrical resistance of the gas sensitive material the composition of a gas or gaseous mixture can be sensed.

Since the electrical resistance of the gas sensitive materials tends also to be temperature dependent, the sensors also preferably include a temperature sensing means. The sensors may also include a heating means to enable operating temperature to be adjusted and/or contaminants to be burnt off if required.

It is to be understood that the sensitivity of a gas sensitive material may depend upon the composition of the gas sensitive materials. Thus, by selection of the composition of the gas sensitive materials their response to a particular gas may be optimized and their response to interferents, such as changes in relative humidity may be minimized.

The resistance may be measured directly. In one preferred embodiment of the present invention, the gas sensitive material has two or more electrodes in communication with said gas sensitive material, and the gas sensitive material and the electrodes are in contact with the same gas.

Preferably the gas sensitive material has porosity to give a satisfactory surface area for contact with the gas or gaseous mixture when in use.

The gas sensitive material, for example, may be prepared from an oxide or from an appropriate precursor. The oxide or precursor may optionally be prepared by a gel process such as a sol-gel process or a gel precipitation process.

The powder may be dried and calcined (e.g. for approximately 16 hours) at a temperature depending upon the particular composition of gas sensitive material being prepared. The product resulting from calcination, which may be in the form of a cake, may be ground as required to give a fine powder. If required, grinding and calcination may be repeated several times in order to obtain a more suitable powder.

Subsequently, the fine powder may be pressed (e.g. with the optional addition of a binder, such as a solution of starch or polyvinyl alcohol) into any suitable shape (e.g. a pellet).

The pressing may be followed by a firing (e.g. at the same temperature as the calcination step(s) described above, or at a somewhat higher temperature, for approximately 16 hours).

In addition to assisting in the binding of the powder into desired shapes, the binder also burns out during the firing stage giving rise to porosity.

As an alternative a powder for subsequent calcination may be prepared, for example, by spray drying a solution (e.g. an aqueous solution) of appropriate starting material (e.g. a metal oxalate, metal acetate or metal nitrate).

Electrodes may be applied to the prepared gas sensitive material in any suitable manner. For example, electrodes (e.g. gold electrodes) may be applied by means of screen printing or sputtering.

A new gas sensing method uses the present air quality monitor invention. First, gas or a gaseous mixture is flowed to the gas sensitive material of the monitor. The gas sensitive material exhibits a response in the form of an increase or a decrease in electrical resistance of the material, which is measured. In a preferred embodiment, the response of the gas sensitive material is measured by electrodes in contact with the material.

Sensors of the monitor are connected to an electrical circuit and a single sign indication of atmospheric impurity is output regardless of whether the impurity gas is of the oxidizing or reducing type. This output may be used to provide quantitative and/or qualitative determinations regarding the gas flowing to the gas sensitive material.

In a preferred embodiment, the temperature is sensed. The monitor may be heated to adjust its operating temperature or to burn off contaminants.

These and further and other objects and features of the invention are apparent in the disclosure, which includes the above and ongoing written specification, with the drawings.

DETAILED DESCRIPTION OF PREFERRED EMBODIMENTS

Figure 1:
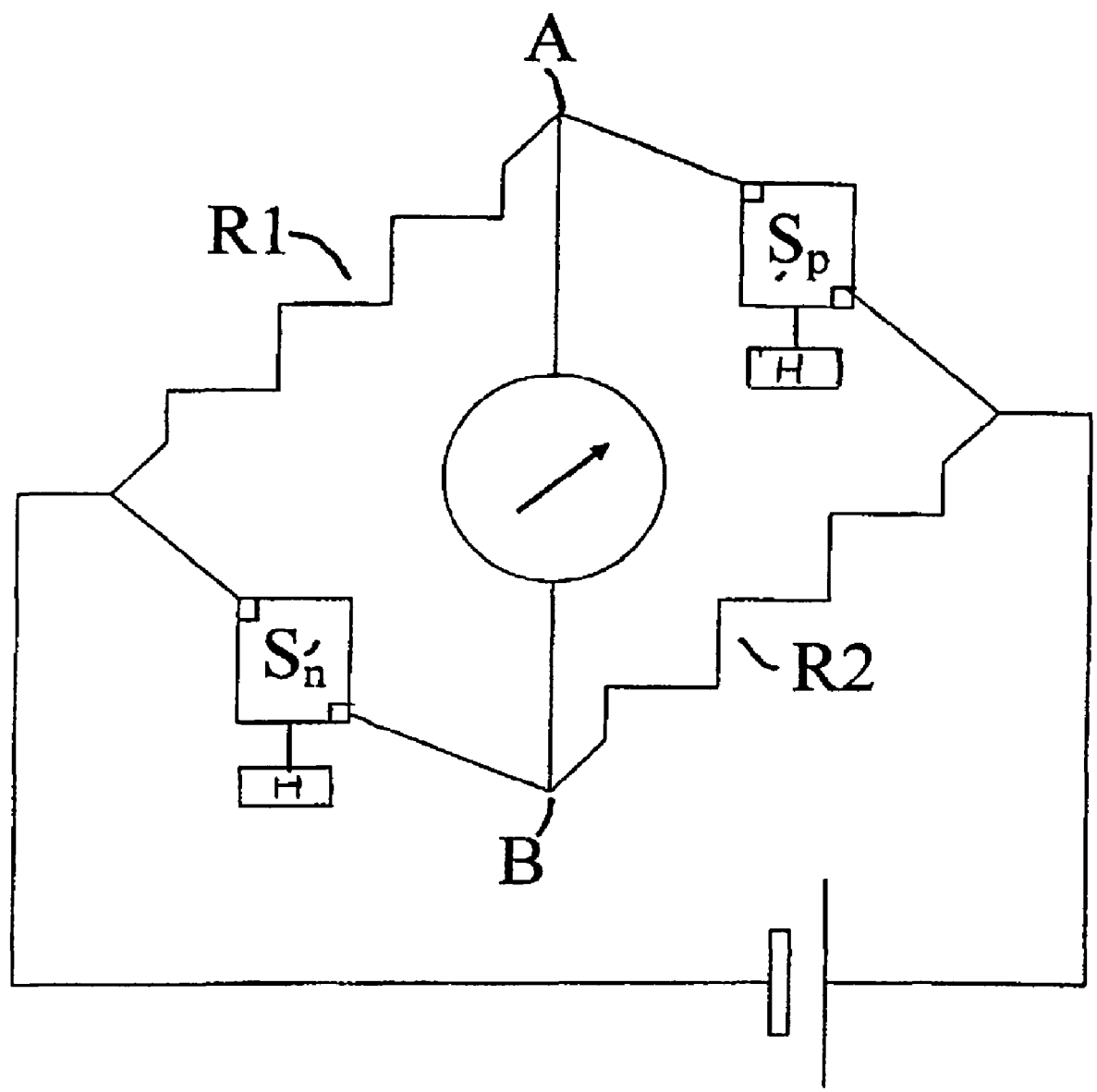
FIG. 1 shows the invention in a Wheatstone bridge circuit.

The present invention provides for a single indication of degraded air quality whether the impurity gas is of the oxidizing type or the reducing type. Preferably, two sensors are used; one for reducing gases and one for oxidizing gases. In a preferred embodiment the sensor for reducing gases is p-type and the sensor for oxidizing gases is n-type so that each sensor provides a resistance increase in the presence of its target gases. The sensors are then connected in opposite arms of a Wheatstone bridge circuit as shown in FIG. 1.

The Wheatstone bridge circuit is for combining the signals from a p-type sensor for reducing gases and an n-type sensor for oxidizing gases into a single indication of air pollution. R1 and R2 are resistors. Sp and Sn are a p-type semiconductor gas sensor and an n-type semiconductor gas sensor, respectively. The meter connecting points A and B registers any out-of-balance condition of the circuit.

The values of the resistors R1 and R2 are selected so that, in clean air, there is zero deflection of the meter that connects points A and B of the circuit. R1 and R2 could, conveniently, be variable resistors. Now, with the n-type and p-type sensors connected as described, the presence of a reducing gas will produce an increase in resistance of the p-type sensor and the presence of an oxidizing gas will produce an increase in resistance of the n-type sensor. In either case the deflection resulting at the meter that connects points A and B will be in the same sense and the output can be viewed as a universal indication of the extent of degradation of air quality.

In an alternative embodiment of the same concept, two n-type sensors could be used but, in this case, the two sensors would have to be deployed in adjacent arms (rather than opposite arms) of the Wheatstone bridge in order to produce a unified air quality output.

In an example of the preferred embodiment of the principle, the n-type sensor disclosed in applicant's earlier patent (U.S. Pat. No. 6,660,231 B2, which is incorporated herein by reference in its entirety) is a good choice for the n-type element of the circuit. Further, chromium oxide doped with titanium oxide may be a possible sensor material for the p-type element. Alternative p-type materials that could be used are the perovskites, $LaFe_{0.95}W_{0.05}O_3$ or $PrFe_{0.95}W_{0.05}O_3$. However, a preferred composition may be, for example, chromium oxide doped with a small amount of a transition element with a higher valence than 4.

EXAMPLES

Examples of one method of preparation of the preferred composition of the materials for the p-type sensor are as follows:

Example 1

36.1 grams of $Cr_2O_3$ and 3.3 grams of $Nb_2O_5$ are mixed with 250 grams of $NaHCO_3$ in an alumina crucible and heated to 900° C. for 10 hours. After cooling the mixture is repeatedly washed with distilled water until no trace of $NaHCO_3$ remains. The dried powder is dispersed in an organic vehicle and screen-printed over gold interdigitated electrodes on an alumina substrate to give an oxide layer thickness of 50 microns. The tiles are previously equipped with a platinum resistance heater on the reverse.

Example 2

36.1 grams of $Cr_2O_3$ and 5.8 grams of $WO_3$ are mixed with 250 grams of $NaHCO_3$ in an alumina crucible and heated to 900° C. for 10 hours. After cooling the mixture is repeatedly washed with distilled water until no trace of $NaHCO_3$ remains. The dried powder is dispersed in an organic vehicle and screen-printed over gold interdigitated electrodes on an alumina substrate to give an oxide layer thickness of 50 microns. The tiles are previously equipped with a platinum resistance heater on the reverse.

While the invention has been described with reference to specific embodiments, modifications and variations of the invention may be constructed without departing from the scope of the invention.

Advantages of the invention include, but are not limited to, the following:

1. The use of one sensor for oxidizing gases and another for reducing gases deployed in the appropriate arms of a Wheatstone bridge circuit so as to provide a single sign of output indicating the presence of an atmospheric impurity of either type.
2. A composition for the sensing material of the p-type sensors comprising chromium oxide, $Cr_2O_3$, doped with a small amount of a transition metal ion having a valence of greater than 4. Examples would be tungsten or niobium.

I claim:

1. An air purity monitor apparatus, comprising:
   a first atmospheric air purity sensor and a second atmospheric air quality sensor wherein the two sensors further comprise one p-type sensor and one n-type sensor, and
   an electrical bridge-type circuit, wherein the first and second sensors are deployed spaced from each other on first and second spaced arms respectively in the electrical bridge-type circuit and the electrical bridge-type circuit provides a unified, single sign indication of atmospheric impurity regardless of whether the impurity gas is of the oxidizing or reducing type.

2. The apparatus of claim 1, wherein the circuit is a Wheatstone bridge circuit.

3. The apparatus of claim 1, wherein the apparatus provides quantitative and/or qualitative determinations regarding gases or gaseous mixtures.

4. The apparatus of claim 1, wherein the sensors further comprise a temperature sensing means.

5. The apparatus of claim 1, further comprising a heating means to enable operating temperature to be adjusted or contaminants to be burnt off.

6. The apparatus of claim 1, wherein each sensor includes a gas sensitive material that exhibits a response in the form of an increase or a decrease in electrical resistance of the material in the presence of a gas and that exhibits a negligible response to changes in the moisture content of the atmosphere.

7. The apparatus of claim 6, further comprising two or more electrodes in communication with the gas sensitive materials, wherein the gas sensitive materials are arranged so as to be capable of being contacted with a gas or gaseous mixture.

8. The apparatus of claim 7, wherein the gas sensitive material and the electrodes are in contact with the same gas.

9. The apparatus of claim 7, wherein the electrodes are applied by means of screen printing or sputtering.

10. The apparatus of claim 6, wherein the resistance of the gas sensitive material is measured directly.

11. The apparatus of claim 6, wherein the gas sensitive material has porosity.

12. The apparatus of claim 6, wherein one of the sensors for reducing gases is a p-type sensor with a gas sensitive material comprising chromium oxide, $Cr_2O_3$, doped with a small amount of a transition metal ion having a valence of greater than 4.

13. The apparatus of claim 6, wherein one of the sensors for reducing gases is a p-type sensor with a gas sensitive material comprising one of the perovskites, $LaFe_{0.95}W_{0.05}O_3$ or $PrFe_{0.95}W_{0.05}O_3$.

14. The apparatus of claim 6, wherein one of the sensors for oxidizing gases is an n-type sensor with a gas sensitive material comprising $W_{0.9}Mo_{0.1}O_3$.

15. The apparatus of claim 6, wherein the gas sensitive material is prepared from an oxide or from an appropriate precursor by:
    drying and calcining a powder at a temperature depending upon the particular composition of gas sensitive material being prepared,
    grinding a product of the drying and calcining as required to give a fine powder,
    repeating grinding and calcination as necessary to obtain a more suitable powder, and
    pressing the fine powder into any suitable shape.

16. The apparatus of claim 15, further comprising firing the shaped powder.

17. The apparatus of claim 16, wherein the firing takes place at the same temperature as the calcination.

18. The apparatus of claim 15, wherein the drying a powder consists of spray drying a solution of appropriate starting material.

19. The apparatus of claim 15, further comprising adding a binder during pressing.

20. The apparatus of claim 19, further comprising firing the shaped powder and burning the binder out, giving rise to porosity.

21. The apparatus of claim 6, wherein the gas sensitive material is prepared from an oxide or from an appropriate precursor comprising gel processing.

22. The apparatus of claim 21, wherein the gel processing comprises sol-gel processing.

23. The apparatus of claim 21, wherein the gel processing comprises gel precipitation processing.

24. The apparatus of claim 6, wherein gas sensing using the apparatus further comprises:
    a conduit flowing gas or a gaseous mixture to the gas sensitive material,
    an electrical circuit connected to the material,
    an electrical source applying power to the electrical circuit,
    a meter measuring a response exhibited by the gas sensitive material in the form of an increase or a decrease in electrical resistance of the material,
    an output from the electrical circuit providing a single sign indication of atmospheric impurity regardless of whether the impurity gas is of the oxidizing or reducing type.

25. The apparatus of claim 24, wherein the meter measuring a response further comprises electrodes contacting the gas sensitive material.

26. The apparatus of claim 24, further comprising an indicator on the meter for providing quantitative and/or qualitative determinations regarding gases or gaseous mixtures.

27. The apparatus of claim 24, further comprising a temperature sensor for sensing the temperature.

28. The apparatus of claim 27, further comprising a heater for heating the apparatus to adjust operating temperature or burn off contaminants.

29. The apparatus of claim 24, wherein the meter for measuring a response further comprises directly measuring the resistance of the gas sensitive material.

30. A method for air purity monitoring, comprising:
    providing an electrical circuit,
    providing a first sensor on a first location on the electrical circuit and sensing atmospheric air purity,
    providing a second sensor on a second location spaced from the first location on the electrical circuit spaced from the first sensor and sensing atmospheric air quality,
    wherein the first and second sensors are deployed spaced from each other on first and second spaced arms respectively in an electrical bridge-type circuit,
    providing a gas sensitive material in each of the first and the second sensors,
    disposing the first sensor and the second sensor with the gas sensitive material in ambient atmosphere to be sensed,
    wherein the two sensors provided in the electric circuit are operable to exhibit a response as an increase or a decrease in electrical resistance of the gas sensitive material in presence of substances in the ambient atmosphere and exhibiting a negligible response to changes in moisture content of the ambient atmosphere,
    measuring fluctuations in the first sensor and the second sensor responsive to presence of substances in the ambient atmosphere, and
    outputting a unified, single sign indication of atmospheric impurity regardless of whether the substances include oxidizing or reducing type gases.

31. The method of claim 1, wherein providing the first and the second sensors further comprise providing p-type sensors.

32. The method of claim 1, wherein providing the first and the second sensors further comprise providing n-type sensors.

33. The method of claim 30, wherein providing the first and the second sensors further comprises providing p-type sensors and n-type sensors.

34. The method of claim 30, wherein providing the first and the second sensors further comprises providing sensors selected from the group consisting of p-type sensors, n-type sensors, and combinations thereof.

\* \* \* \* \*